(12) United States Patent
Noras

(10) Patent No.: US 11,246,575 B2
(45) Date of Patent: Feb. 15, 2022

(54) BIOPSY NEEDLE GUIDE WITH POINTER FOR SIMPLIFIED ANGULATION

(71) Applicant: Hubert Noras, Wurzburg (DE)

(72) Inventor: Hubert Noras, Wurzburg (DE)

( * ) Notice: Subject to any disclaimer, the term of this patent is extended or adjusted under 35 U.S.C. 154(b) by 395 days.

(21) Appl. No.: 16/488,255

(22) PCT Filed: Feb. 9, 2018

(86) PCT No.: PCT/DE2018/100112
§ 371 (c)(1),
(2) Date: Aug. 23, 2019

(87) PCT Pub. No.: WO2018/157883
PCT Pub. Date: Sep. 7, 2018

(65) Prior Publication Data
US 2020/0000443 A1  Jan. 2, 2020

(30) Foreign Application Priority Data

Mar. 1, 2017 (DE) .................... 10 2017 104 302.0

(51) Int. Cl.
| | |
|---|---|
| *A61B 10/00* | (2006.01) |
| *A61B 10/02* | (2006.01) |
| *A61B 17/34* | (2006.01) |
| *A61B 90/11* | (2016.01) |
| *A61B 90/00* | (2016.01) |
| *A61B 10/04* | (2006.01) |

(52) U.S. Cl.
CPC ...... *A61B 10/0233* (2013.01); *A61B 17/3403* (2013.01); *A61B 90/11* (2016.02); *A61B 90/39* (2016.02); *A61B 2010/045* (2013.01); *A61B 2017/3413* (2013.01)

(58) Field of Classification Search
CPC . A61B 10/0233; A61B 17/34; A61B 17/3403; A61B 2010/045; A61B 2017/3407; A61B 2017/3413; A61B 2090/395; A61B 90/11; A61B 90/39
See application file for complete search history.

(56) References Cited

U.S. PATENT DOCUMENTS

2014/0330277 A1* 11/2014 Ogrodnik ........... A61B 17/1725
606/87

FOREIGN PATENT DOCUMENTS

DE   102013113277 A1   6/2015
EP       2090687 A1   11/2016
(Continued)

*Primary Examiner* — Mark D Remaly
(74) *Attorney, Agent, or Firm* — DP IP Group; Franco S. De Liguori

(57) ABSTRACT

Biopsy needle guide with pointer for performing a biopsy in a tissue of a patient in conjunction with an imaging method for imaging the tissue and identification of a target volume to be examined, comprising a needle guide head (2), which is freely movable in a plane via at least two degrees of freedom and is mounted so as to be movable about an axis (S) that does not stand perpendicular to this plane, and has a needle passage opening (20, 29), a marker pin (4), which can be inserted in an opening (20, 29) of the head (2) and contains a marker part (41), which can be imaged by the imaging method with good contrast, wherein, when the marker pin (4) is inserted in the opening (20, 29), the marker part (41) lies in the pivot axis (S) of the head (2), as well as a use of such a biopsy needle guide.

11 Claims, 2 Drawing Sheets

(56) References Cited

FOREIGN PATENT DOCUMENTS

GB 2493429 A 2/2013
WO WO 2017025653 2/2017

* cited by examiner

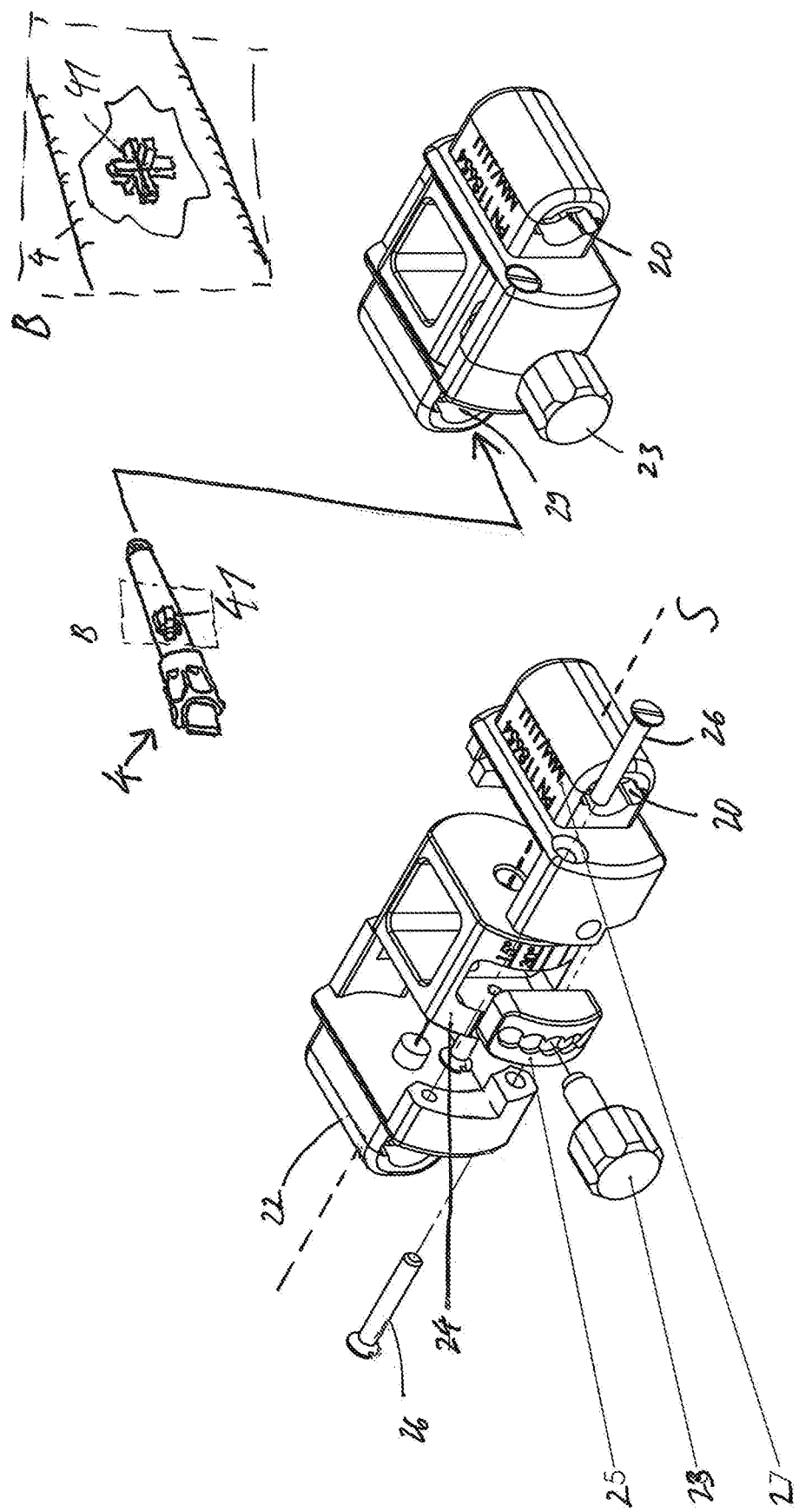

BIOPSY NEEDLE GUIDE WITH POINTER FOR SIMPLIFIED ANGULATION

The present invention relates to a biopsy needle guide with pointer for performing a biopsy in a tissue of a patient in conjunction with an imaging method for imaging the tissue and identification of a target volume to be examined, comprising a needle guide head, which is freely movable in a plane via at least two degrees of freedom and is mounted so as to be freely pivotable about an axis that does not stand perpendicular to this plane, and has a needle passage opening, a marker pin, which can be inserted in an opening of the head and contains a marker part, which can be imaged by the imaging method with good contrast, as well as a use of such a biopsy needle guide.

By biopsy is meant the targeted removal of a small tissue sample from the body of a patient. For this purpose, biopsy needles are used in general, of which the tip, after insertion at a point on the body surface that is often as close as possible to the tissue to be examined, is pushed into the target volume in the tissue, where a tissue sample is then taken, before the needle is removed again. To be able to ensure a neat, precise insertion, a mechanical needle guide is used here, which holds the biopsy needle and stabilizes it in a lateral direction, such that a movement of the needle is only possible in an axial direction. For free positioning and selection of the insertion point and direction, the actual needle guide opening is introduced into a guide head, which can be traversed by a certain distance, in a plane, via at least two degrees of freedom.

A problem almost always occurring in biopsies is to reliably hit a target volume disposed in the interior of the patient's body. In general, this is only possible with the use of an imaging process, which images the target volume and biopsy needle or needle guide, and can visually represent their spatial relationship. This method can, for example, be ultrasound, computer tomography or magnetic resonance tomography. Since for reasons of the imaging quality, the needle guide is made of material that is largely transparent for the imaging method in each case, and the biopsy needle, as an extensive object, makes exact localization difficult, marking aids or pointers are used, which mark a reference point on the images.

The simplest procedure known in the prior art is to represent markers and target volume on an image with an image plane perpendicular to the insertion direction. An operator of the needle guide then only needs to position the needle guide head such that markers or pointers are congruent with the target volume. Then, it is guaranteed that a straight-line insertion along the direction from imaging focus to image point(s) of the target volume, that is to say essentially perpendicular to the image plane, must guide the needle tip through the target volume.

The depth information, which is further required, that is to say the perpendicular distance between the traverse plane of the needle guide head and the target volume, can be determined from one or more additional imagings, which are recorded in a plane that is not parallel to the first imaging plane. For reasons of simplicity, if possible, image planes that are perpendicular to the first plane are usually chosen. This makes the determination of the desired distance particularly simple, since it can then be easily dimensioned directly from this image.

A disadvantage of this simple procedure, however, is that an insertion by a direct route is not always possible or medically advisable. First, there may be bone, cartilage or other comparatively hard tissue between the direct insertion point and target volume, which would be hardly possible, or at least very imprecise, to penetrate with a biopsy needle, quite apart from the tissue traumas produced by such a biopsy. Also, or additionally, there may be particularly sensitive tissue on the direct insertion route, for example blood vessels or nerves, which it is preferable, or essential, to avoid. Depending on the anatomical conditions, for example in the case of a biopsy of the female breast, the direct insertion route may run through tissue to an unnecessary extent.

In all these cases, it is appropriate to deviate from the straight-line insertion route, which is directed along the rays from the imaging focus to the target volume. To allow this, in the prior art, needle guides are used which permit an additional pivoting of the needle guide head by one or two axes. Such needle guides are disclosed, for example, in German patent DE 10 2013 113 277 A1.

However this results in the difficulty of correct angulation. This first comprises the subproblem, for a given, desired angular settings of the correct receiving point of the needle guide head, that is to say that/those point(s) of the traversing range, often a plane, onto which the needle guide head or more precisely the passage opening of the head used for introducing the needle, is to be brought, so that, for the given angular settings, the target volume is located on the insertion path of the needle.

Since only a few people can easily or rapidly solve this trigonometric task in their head, technical aids are required for this. The solutions known in the prior art use, for this purpose, a software that, possibly in conjunction with a computer-aided image evaluation of the images obtained by means of the imaging process, can compute the correct receiving point and, from this, in a second step, the traverse position of the head. As an input, it is necessary to determine the position of the target volume in the coordinate system of the needle guide. From this, the desired receiving point can then be determined as that, or those, point(s) of a straight line through (a point, approximately the centre) of this target volume with a direction vector that is determined by the desired angular settings, with the traverse plane or the traverse range of the needle guide head. The head is then to be traversed such that the passage opening of the head comes to lie at the receiving point thus determined.

The settings that are to be specifically made by the operator of the needle guide result from this, however, in general only after a second computation step, in which the known geometric dimensions of the needle guide head are taken into account in order to determine the correct traversing position from the receiving point and the desired angular settings. This second subproblem of angulation is more computationally complicated than the determination of the receiving point, depending on the available degrees of freedom and design of the head, and therefore requires technical support by the user to a greater extent.

However, the use of a software for automation of the positioning computations has the consequence that the entire system, comprising needle guide, image evaluation and positioning software, is much more complicated to create than only the needle guide itself. This results in a significant cost increase. In addition, with the software, an additional error source is introduced. This does not affect the correct functioning of the software itself, which is naturally also to be ensured by verification and validation, so much as the interaction between the user and the software. In the case where the operation is confusingly or awkwardly designed, faulty inputs may occur, which result in incorrect positioning.

In addition, due to the necessary interaction of the operator with the software, the biopsy operation as a whole is significantly slowed.

It is therefore the object of the present invention to develop a biopsy needle guide, which permits a simple, rapid, reliable and less faulty angulation even without automation.

This object is achieved by means of a biopsy needle guide according to the independent claim 1, which, according to the invention, is used according to the independent claim 10.

The needle guide according to the invention is herein simplified to the extent that an angulation by an experienced user without technical aids is possible by means of the imaging method used for imaging the tissue to be examined. To this end, as essential points, the construction and the ergonomics of operation of the needle guide head were optimized. This cooperates in a synergistic manner to achieve the object.

First, the head of the needle guide according to the invention is equipped with an opening for receiving a marker pin and is designed so that it can be traversed in a plane and can be pivoted about at least one axis. The marker pin accommodates in its interior a marker part, which can be sharply imaged with good contrast by means of the imaging method used. The marker part forms a reference point, with the aid of which the relative spatial position of the target volume and needle guide head can be determined. To avoid a movement of this reference point, that is to say the marker part of the marker from the traverse plane of the head, the pivot axes of the head lie in the traverse plane and have a common intersection point with the axis defined by the opening. The marker pin is then constructed such that the marker part comes to lie with its centre point as accurately as possible in this intersection. It is thus advantageously achieved that the reference point formed by the marker part is independent of the pivot state, that is to say the chosen pivot angles of the head, and thus remains stationary. The above-described, more difficult second subproblem is essentially eliminated due to the advantageous design according to the invention of the needle guide head.

At the beginning of the use, according to the invention of this biopsy needle guide, is first the stationary placement and attachment of the needle guide over the patient's body region that is to be examined. The needle guide head, unless this has not already been done, is brought into a basic or starting position and the marker pin according to the invention is completely inserted into an opening of the head.

Then, the images that are required to determine the relevant information are produced. This requires at least an imaging on which the target volume in the tissue to be examined, such as a tissue part that appears to have changed in a suspect way can be identified and/or localized. It should be noted that both the target volume and that marker part of the marker according to the invention that serves as reference point are imaged simultaneously, so that the relative spatial position of the marker part and target volume can be determined. To this end, at least two illustrations in different, non-parallel image planes are necessary, for example one perpendicular to a main direction and one containing this main direction. The main direction depends on the position of the region in the body that is to be examined. This may be the ventral-dorsal direction in the case of examinations of the torso or the cranial-caudal direction in the case of examinations of the pelvis. The coordinates of the target volume in the coordinate system defined by the needle guide are to be determined. This comprises, on one hand, the distance of the target volume from the traverse region or traverse plane of the needle guide head and, on the other, the base point for this distance determination, that is to say the intersection point of a line, perpendicular to the traverse plane, through the target volume with the traverse plane.

If these are known, the target position of the reference point in the traverse plane can be determined from the desired angular settings and the head can be moved to the corresponding point and pivoted as desired. The marker pin is then replaced by a sterile adapter sleeve for guiding the needle and the needle is introduced. On introduction into the body, the needle tip is pushed beyond the reference point as far as corresponds to the calculated distance between the reference point and target volume. Once this has taken place, the needle tip of the biopsy needle is, with very high confidence, located in the intended target volume. The removal of an informative sample is thus possible.

The obvious advantages of the needle guide presented by the present invention and its use are a considerable simplification and speeding up of the angulation process, since no coupling is provided between the pivot state and position of the reference point that is visible to the operator in the images. If the receiving point is known, the traverse position of the head is determined from it almost directly, only a possible offset between the setting scale of the translatory degrees of freedom of the head and the opening that is used specifically for passing through the needle needs to be taken into account. If this is chosen such that it is fixed, it can be taken into account when the scales are created. Alternatively, it would be conceivable to design the scale marking such that it is movable, so that, with a changing passage opening, each of the scales only has to be shifted by a corresponding correction amount, to achieve the read-off values corresponding directly to the coordinates of the opening used.

As a further indirect advantage, this has the result that the number of error sources would be reduced. Complicated conversions between the receiving point and the coordinate setting to be chosen are no longer necessary. Software is thus also unnecessary.

Arbitrary angles, even with pivoting between two axes, can also be taken into account. The receiving point is then determined from $x_i = x_i^{zv} - d \tan(\alpha_i)$, where $x_i$ is the i-th coordinate, $x_i^{zv}$ the value of the i-th coordinate for the target volume, d is the determined distance between the traverse plane and target volume, and $\alpha_i$ the relevant angle set for the i-th coordinate.

Advantageous embodiments of the present invention, which can be realized individually or in combination, in so far as they do not obviously preclude one another are described below.

The needle guide head of the biopsy needle guide according to the invention preferably comprises a plurality of passage openings, of which at least one is suitable for inserting the marker pin according to the invention and another for inserting an adapter sleeve, these two openings having in each case an intersection point with the pivot axis of the head.

The adapter sleeve and the marker pin particularly preferably have similar and dimensioned shafts, such that they are compatible with the same openings. By this means, it can be freely chosen which opening should serve for receiving the marker pin and which for receiving the biopsy needle. This can be suitably be used for the configuration of the needle guide according to the invention appropriate for left-handed or right-handed persons.

The marker part accommodated in the marker pin, which actually creates the visual reference point preferably has a cross- or cross-hair-shaped cross-section. In comparison to a simple circular or square cross-section, for the same surface area, this permits a considerably more accurate visual localization of the reference point on the images generated by means of the imaging process used. The marker part according to the present invention should ideally have such a cross-section not only in one but in two, or even three, planes that are perpendicular to one another. It is thus achieved that the advantageously increased localization accuracy is achieved, even in the case of images of which the image planes are not determined by the main direction but essentially perpendicular thereto.

To ensure sufficient visibility of the marker part on the images, the marker part must be of sufficient size, for which reason the diameter of the marker opening is chosen by the present invention to be sufficiently larger and significantly larger than passage openings known in the prior art. The marker part and thereby also the marker pin enclosing it thus still have a diameter, that is to say a shank diameter, that is considerably larger than the diameter of a biopsy needle. The diameter is preferably 2-4 times that of a biopsy needle. By this means a significant visibility of the images generated by means of the imaging method is ensured. Thanks to the cross(-hair)-like structure according to the invention, even with such a size, an accurate position determination of the reference point is possible. This further considerably increases the precision of the angulation.

In order to simplify the first subproblem, that is to say the determination of the receiving point in the traverse region of the needle guide head, the present invention proposes providing only a limited number of angular settings. It has proven particularly effective to provide the pivoting or the pivoted fixing of the needle guide head in discrete steps of 15 degrees. A suitable pivot range here is from +30 to −30 degrees relative to a neutral position, in which the longitudinal directions of the openings of the head are perpendicular to the traverse plane. Particularly preferably, the pivot range from +60 to −60 degrees is sufficient.

The settings +45 and +60 degrees are here particularly interesting. Since $\tan(45°)=1$ applies, in the first case the determination of the receiving point coordinates reduced to an addition or subtraction of the determined distance d between the target volume and traverse plane from the coordinate values of the target volume. This can easily be calculated in one's head. The distance between the reference point and target volume is then simply ca. $1.41*d$.

In the second case, the distance determination is simplified, as, since $\cos(60°)=½$, the "known" distance d between the target volume and traverse plane corresponds to exactly half of the distance between the target volume and receiving point. The offset of the receiving point with respect to the target volume coordinates can be determined by addition/subtraction by approximately $0.85*d$.

The present invention further proposes preferred embodiments in which the head has two translatory degrees of freedom, which permits movement in one plane. This is implemented such that the head can be traversed on a guide carrier, which is in turn seated on a carriage, which slides on a rail oriented perpendicular to the longitudinal direction of the guide carrier. The carriage as well as the head can be fixed in the desired positions by means of fixing means, in particular clamping screws. The head can hereby particularly preferably also be fixed in the pivoted condition, at least in discrete steps of 15 degrees between preferably −30 and +30 degrees, particularly preferably between −60 and +60 degrees.

With the use of the biopsy needle guide according to the invention, an embodiment with a plurality of openings is preferably used, so that the marker pin and biopsy needle can be used simultaneously. The above-described procedure would then have to be modified such that, on determination of the traverse position of the head, the known distance between the reference point and adapter sleeve opening is also taken into account, that is to say the head is then displaced by the corresponding distance. It is then no longer necessary to remove the marker pin only before passing through the needle and to use the adapter sleeve instead.

Further properties, features and advantages of the present invention are described in greater detail below with reference to exemplary embodiments explained in detail in the appended figures. These are only intended to illustrate the invention, and in no way to limit its generality.

wherein:

FIG. 2 shows an exploded view and a perspective view of the head as well as of the marker pin from FIG. 1.

Figure 1:
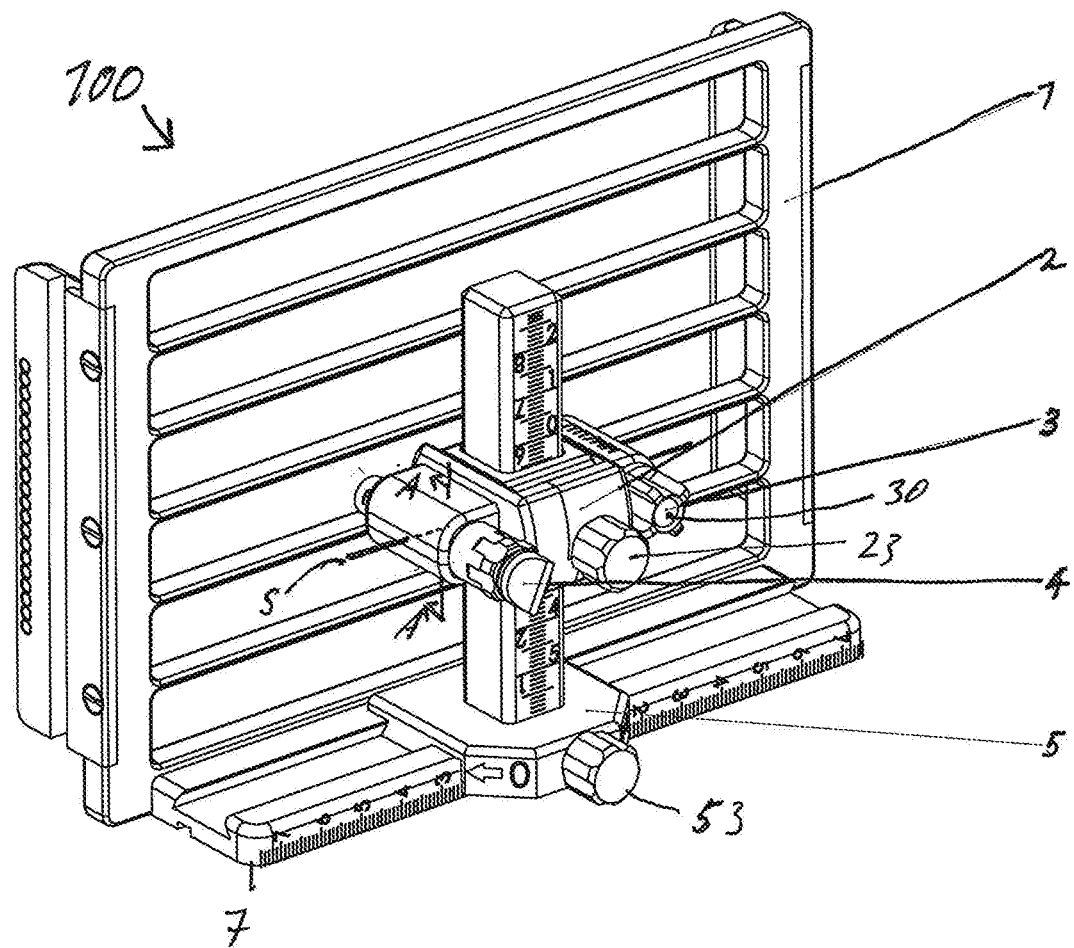
FIG. 1 shows a perspective view of an embodiment of the biopsy needle guide according to the invention.
Figure 1:
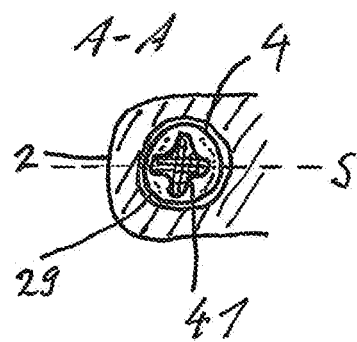

FIG. 1 shows a perspective view of a preferred embodiment of the biopsy needle guide according to the invention. Needle guide 100 consists of the grid-like frame 1 with rail 7, with is mounted projecting on the underside, on the carriage 5, which is guided in a straight line such that it is movable. Carriage 5 can be fixed by means of clamping screw 53 at an arbitrary place of rail 7. On carriage 5, a guide carrier 6 is mounted perpendicular to rail 7; the guide carrier 6 movably bears needle guide head 2, which, by means of clamp screw 23, can be fixed at any position on guide carrier 6. Head 2 is thus freely positionable and fixable via two translatory degrees of freedom in the movement plane defined by the rail 7 and guide carrier 6. Both the rail 7 and guide carrier 6 have scale divisions that permit precise positioning within the reading accuracy.

Head 2 comprises two openings 20, 29 for receiving, in each case, optionally marker pin 4 or adapter sleeve 3; marker pin 4 here being represented inserted in the left opening 29 and adapter sleeve 3 in the right opening 20. Marker pin 4 and adapter sleeve 3 thus have identical shank diameters. This diameter is chose such that it corresponds to a multiple of, in this case three times, the diameter of a biopsy needle, which is calculable from opening 30 in adapter sleeve 3. In the case of adapter sleeve 3, this helps to provide an adequate spatial separation for guaranteeing a sterile insertion and extraction of the biopsy needle. For marker pin 4, a larger diameter is advantageous because the use of a larger marker part, which defines the actual reference point, is thus possible. By means of a corresponding shaping of the marker part, the loss of localization accuracy, which is otherwise to be expected by an enlargement of the cross-section, can be more than compensated.

Section A-A shows a cross-section through the left portion of head 2, the intersection plane containing the pivot axis S of head 2. It shows the circular cross-section of the shank of marker pin 4 and the marker part 41 with cross-shaped cross-section in its interior. Marker part 41, which defines the actual reference point for an operator of the biopsy needle guide according to the invention, when marker pin 4 is inserted, lies exactly in the pivot axis S of head 2. A disadvantageous coupling of the pivot state of head 2 and the position of the reference point, that is to say marker part 41, is thus avoided, which permits a rapid, easy and precise angulation.

FIG. 2 shows an exploded view and a perspective detail view of the needle guide head and of the marker pin of the needle guide from FIG. 1.

The left-hand partial figure shows an exploded view of needle guide head 2. As illustrated, it consists of three main components: a left portion 22 and a right portion 27, of which each comprises an opening 20, 29, and which, via pins, are mounted in a central body 24, in openings lying concentric to the pivot axis S. The portions 22, 27 are also firmly connected together via screws 26. Index plate 25 is inserted in a depression on the front side of body 24 and has five holes that merge with one another for indexing the clamping positions. In conjunction with clamping screw 23, which is guided in a screw thread formed by the left and right portions 22, 27, it permits the head to be clamped in five different angular positions. These correspond to a pivotability of the needle guide head in a range from −30 to −30 degrees in 15-degree steps.

The right-hand partial figure shows the head assembled again in perspective view, as well as the marker pin 4 from FIG. 1. This has, in its interior, marker part 41 with cross-shaped cross-section, which, when marker pin 4 is completely inserted into one of the openings 20, 29, comes to lie precisely in the pivot axis S of needle guide head 2.

Detail view B shows a section of the shank of marker pin 4 cut open, so that marker part 41 can be seen enlarged again. In this embodiment, it has a cross-shaped cross-section, not only in one sectional plane, but in three mutually perpendicular sectional planes. By this means, the advantageously improved localizability, which is achieved by this shaping also comes into effect in the case of images of which the image planes are not defined by the longitudinal direction of the marker.

LIST OF REFERENCE CHARACTERS

1 Frame
2 Needle guide head
20 Passage opening
22 Left portion
23 Clamp screw
24 Corpus
25 Index plate
26 Screw
29 Passage opening
3 Adapter sleeve
4 Marker pin
41 Marker part
100 Biopsy needle guide
S Pivot axis

The invention claimed is:

1. A biopsy needle guide with pointer for performing a biopsy in a tissue of a patient in conjunction with an imaging method for imaging the tissue and identification of a target volume to be examined, comprising:
a needle guide head, which is freely movable in a plane via at least two degrees of freedom and is mounted so as to be pivotable about an axis that does not stand perpendicular to this plane, and has a needle passage opening, and
a marker pin, which can be inserted in the opening of the head and contains a marker part, which can be imaged by the imaging method with good contrast,
wherein when the marker pin is inserted in the opening of the head, the marker part lies in the pivot axis of the head.

2. The biopsy needle guide according to claim 1, wherein in the head a plurality of openings suitable for inserting the marker pin are present, of which at least two have an intersection point with the pivot axis of the head.

3. The biopsy needle guide according to claim 2, characterised in that an adapter sleeve inserted into the opening is present.

4. The biopsy needle guide according to claim 1, wherein in a sectional plane, the marker part has a cross-shaped or cross-hair-shaped cross-section.

5. The biopsy needle guide according to claim 4, wherein the marker part has, in at least one further sectional plane, which is not parallel to the first plane and is in particular perpendicular thereto, a cross-shaped or cross-hair-shaped cross-section.

6. The biopsy needle guide according to claim 1, wherein a diameter of the marker pin is significantly larger than a diameter of the biopsy needle.

7. The biopsy needle guide according to claim 1, wherein the head has two translatory degrees of freedom, in particular in that the head is linearly movable on a guide support, which, in turn, is mounted on a slide, which is traversable on a rail, which is essentially perpendicular to the longitudinal axis of the guide support.

8. The biopsy needle guide according to claim 7, wherein the head has a fixing means, by means of which it can be fixed on the guide support, in particular also such that it is pivoted out of a neutral position.

9. The biopsy needle guide according to claim 8, wherein the fixing means is a clamp screw, by means of which the head can be clamped such that it pivots in 15 degree steps between at least +30 degrees and −30 degrees about the neutral position.

10. A method of using a biopsy needle guide with pointer for biopsy of a tissue of a patient's body region to be examined in conjunction with an imaging method for imaging the tissue and the pointer, the method comprising:
(a) providing a biopsy needle guide with pointer, comprising: a needle guide head that is freely movable in a plane via at least two degrees of freedom and is mounted so as to be pivotable about an axis that does not stand perpendicular to this plane, the head having needle passage openings; and a marker pin, which can be inserted in an opening of the head and contains a marker part, which can be imaged by the imaging method with good contrast; wherein when the marker pin is inserted in the opening, the marker part lies in the pivot axis of the head;
(b) placing the biopsy needle guide over the region to be examined and suitably fastening the biopsy needle guide to the region to be examined;
(c) moving the head, if necessary, into a basic position, and completely inserting the marker pin into one of the openings of the head;
(d) generating a necessary number of images by means of the imaging method for identifying and/or localizing a target volume, including imaging and generating a sufficient number of images of marker part;
(e) determining, from the generated number of images, a target volume and its coordinates of the biopsy needle guide, including a spacing from a movement range or a traverse plane of the head, and displaying to an operator at least a visual representation conveying the relative position of the target volume and marker part of the marker pin;
(f) taking into account resulting anatomical circumstances and a desired pivot angle, determining a receiving point for a biopsy needle within the traverse range or the traverse plane of the head and the distance of this receiving point to the target volume;

(g) traversing the head such that the marker part comes to lie at the determined receiving point, and adjusting the desired pivot angle;
(h) removing and replacing the marker pin by an adapter sleeve for guiding the biopsy needle;
(i) introducing the biopsy needle by a stretch that corresponds to the determined distance between the receiving point and target volume; and
(j) taking a sample of the tissue of the patient's body region.

11. A method of using a biopsy needle guide with pointer for biopsy of a tissue of a patient's body region to be examined in conjunction with an imaging method for imaging the tissue and the pointer, the method comprising:
(a) providing a biopsy needle guide with pointer, the biopsy needle guide comprising: a needle guide head that is freely movable in a plane via at least two degrees of freedom and is mounted so as to be pivotable about an axis that does not stand perpendicular to this plane, the head having a plurality of needle passage openings at least two of which have an intersection point with a pivot axis of the head; and a marker pin, which can be inserted in the openings of the head and contains a marker part, which can be imaged by the imaging method with good contrast; wherein when the marker pin is inserted in the opening, the marker part lies in the pivot axis of the head;
(b) placing the biopsy needle guide over the region to be examined and suitably fastening the biopsy needle guide to the region to be examined;
(c) moving the head, if necessary, into a basic position, and completely inserting the marker pin into one of the openings of the head and inserting an adapter sleeve into another opening of the head;
(d) generating a necessary number of images by means of the imaging method for identifying and/or localizing a target volume, including imaging and generating a sufficient number of images of marker part;
(e) determining, from the generated number of images, a target volume and its coordinates of the biopsy needle guide, including a spacing from a movement range or a traverse plane of the head, and displaying to an operator at least a visual representation conveying the relative position of the target volume and marker part of the marker pin;
(f) taking into account resulting anatomical circumstances and a desired pivot angle, determining a receiving point for a biopsy needle within the traverse range or the traverse plane of the head and the distance of this receiving point to the target volume;
(g) taking into account the known distance between the intersecting points of the pivot axis with the opening used, traversing the head such that the intersecting point of the pivot axis comes to lie with the adapter sleeve opening in the determined receiving point;
(h) introducing the biopsy needle by a stretch that corresponds to the determined distance between the receiving point and target volume; and
(i) taking a sample of the tissue of the patient's body region.

* * * * *